(12) United States Patent
Smith et al.

(10) Patent No.: US 9,995,685 B2
(45) Date of Patent: *Jun. 12, 2018

(54) METHOD FOR OPTICAL DETECTION OF SURVEILLANCE AND SNIPER PERSONNEL

(71) Applicants: Jeffrey Michael Smith, Pembroke, MA (US); Gerald Edwin Bender, Youngsville, NC (US); Roger D. Whitmer, Pittsfield, MA (US); Patrick T. Toohey, Falls Church, VA (US)

(72) Inventors: Jeffrey Michael Smith, Pembroke, MA (US); Gerald Edwin Bender, Youngsville, NC (US); Roger D. Whitmer, Pittsfield, MA (US); Patrick T. Toohey, Falls Church, VA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/340,685

(22) Filed: Nov. 1, 2016

(65) Prior Publication Data

US 2017/0299520 A1 Oct. 19, 2017

Related U.S. Application Data

(63) Continuation of application No. 13/913,333, filed on Jun. 7, 2013, now Pat. No. 9,482,617.

(60) Provisional application No. 61/689,514, filed on Jun. 7, 2012.

(51) Int. Cl.
| | | |
|---|---|---|
| *F21V 9/16* | (2006.01) |
| *G01N 21/64* | (2006.01) |
| *G01S 17/02* | (2006.01) |
| *G01S 7/48* | (2006.01) |
| *G01S 7/487* | (2006.01) |
| *G01S 17/89* | (2006.01) |
| *G01S 17/10* | (2006.01) |

(52) U.S. Cl.
CPC ........ *G01N 21/6486* (2013.01); *G01S 7/4802* (2013.01); *G01S 7/4876* (2013.01); *G01S 17/02* (2013.01); *G01S 17/89* (2013.01); *G01S 17/026* (2013.01); *G01S 17/107* (2013.01)

(58) Field of Classification Search
CPC .......................... A61B 3/1225; A61B 3/125
See application file for complete search history.

(56) References Cited

U.S. PATENT DOCUMENTS

| | | | |
|---|---|---|---|
| 7,282,695 | B2 | 10/2007 | Weber et al. |
| 7,456,944 | B2 | 11/2008 | Haan et al. |
| 7,858,920 | B2 | 12/2010 | Duvent et al. |
| 7,978,330 | B2 | 7/2011 | Reyes, Jr. et al. |
| 8,063,348 | B1 | 11/2011 | Swaminathan |
| 8,132,491 | B2 | 3/2012 | Real |
| 8,228,591 | B1 | 7/2012 | Towers |
| RE43,681 | E | 9/2012 | Wild |

(Continued)

*Primary Examiner* — Kenneth J Malkowski
(74) *Attorney, Agent, or Firm* — Schmeiser, Olsen & Watts, LLP

(57) ABSTRACT

A method comprising: providing a device for detecting a biological signature behind a glass surface using non-visible light is provided. A method of emitting one or more pulses of energy at a specific wavelength over a field of illumination towards a target area, filtering out one or more returning wavelengths from the target area, and determining, based on the filtering, if a combination of a fluorescence wavelength and a source wavelength is present, is also provided. An associated system is further provided.

18 Claims, 7 Drawing Sheets

(56) References Cited

U.S. PATENT DOCUMENTS

| | | | |
|---|---|---|---|
| 8,994,819 B2 * | 3/2015 | Bennett | G01S 17/026 348/143 |
| 9,482,617 B2 | 11/2016 | Smith et al. | |
| 2006/0228003 A1 | 10/2006 | Silverstein | |
| 2010/0128992 A1 | 5/2010 | Duvent et al. | |
| 2012/0229768 A1 | 9/2012 | Gramatikov | |

* cited by examiner

METHOD FOR OPTICAL DETECTION OF SURVEILLANCE AND SNIPER PERSONNEL

CROSS-REFERENCE TO RELATED APPLICATIONS

This non-provisional application is a continuation application of U.S. application Ser. No. 13/913,333, filed Jun. 7, 2013, issued Nov. 1, 2016 as U.S. Pat. No. 9,482,617 entitled, "Method for Optical Detection of Surveillance and Sniper Personnel," which claims priority to U.S. provisional application No. 61/689,514, filed Jun. 7, 2012, and entitled "Method for Optical Detection of Surveillance and Sniper Personnel."

FIELD OF TECHNOLOGY

The following relates to the optical detection of reflected wavelengths, and more specifically to embodiments of a system and method for detecting a dual wavelength return unique to a sniper eye and scope combination.

BACKGROUND

Effective sniper detection systems are currently highly sought after due to their ability to save the lives of individuals at risk for sniper attack. Various systems are currently in use to detect and locate a sniper threat. For instance, some systems trace the acoustic signature of the gunshot, or attempt to locate a source of gunfire by detecting a muzzle flash. Each of these approaches suffers the defect of not being able to locate or even identify the risk of a sniper until after at least one shot has been fired. Oftentimes, this is too late for effective protection of the individuals relying on the detection system. Moreover, other optical systems have been used in an attempt to detect and locate a sniper threat, but these methods and systems have proven unreliable and inadequate when it comes to filtering the various reflected wavelengths.

Thus, a need exists for an apparatus and method for detecting and locating a sniper threat by detecting a unique retroreflection signature generated by the combination of an optic system/scope with the human eye behind it.

SUMMARY

A first aspect relates generally to a method comprising providing an energy source and an image processing device for detecting a biological signature behind a glass surface using non-visible light.

A second aspect relates generally to a method comprising detecting a unique dual wavelength, the unique dual wavelength resulting from one or more pulses of energy in a field of illumination, wherein the unique dual wavelength is a combination of a fluorescence wavelength and a source wavelength.

A third aspect relates generally to a method comprising emitting one or more pulses of energy at a specific wavelength over a field of illumination towards a target area, filtering out one or more returning wavelengths from the target area, and determining, based on the filtering, if a combination of a fluorescence wavelength and a source wavelength is present.

A fourth aspect relates generally to a system comprising an energy source for emitting one or more pulses of energy at a specific wavelength over a field of illumination towards a target area, an image processing device having a first image processing device for receiving a returned source wavelength, and a second image processing device for receiving a returned fluorescence wavelength, wherein the image processing device determines if both the returned source wavelength and the returned fluorescence wavelength are present while scanning the target area.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figure 1:
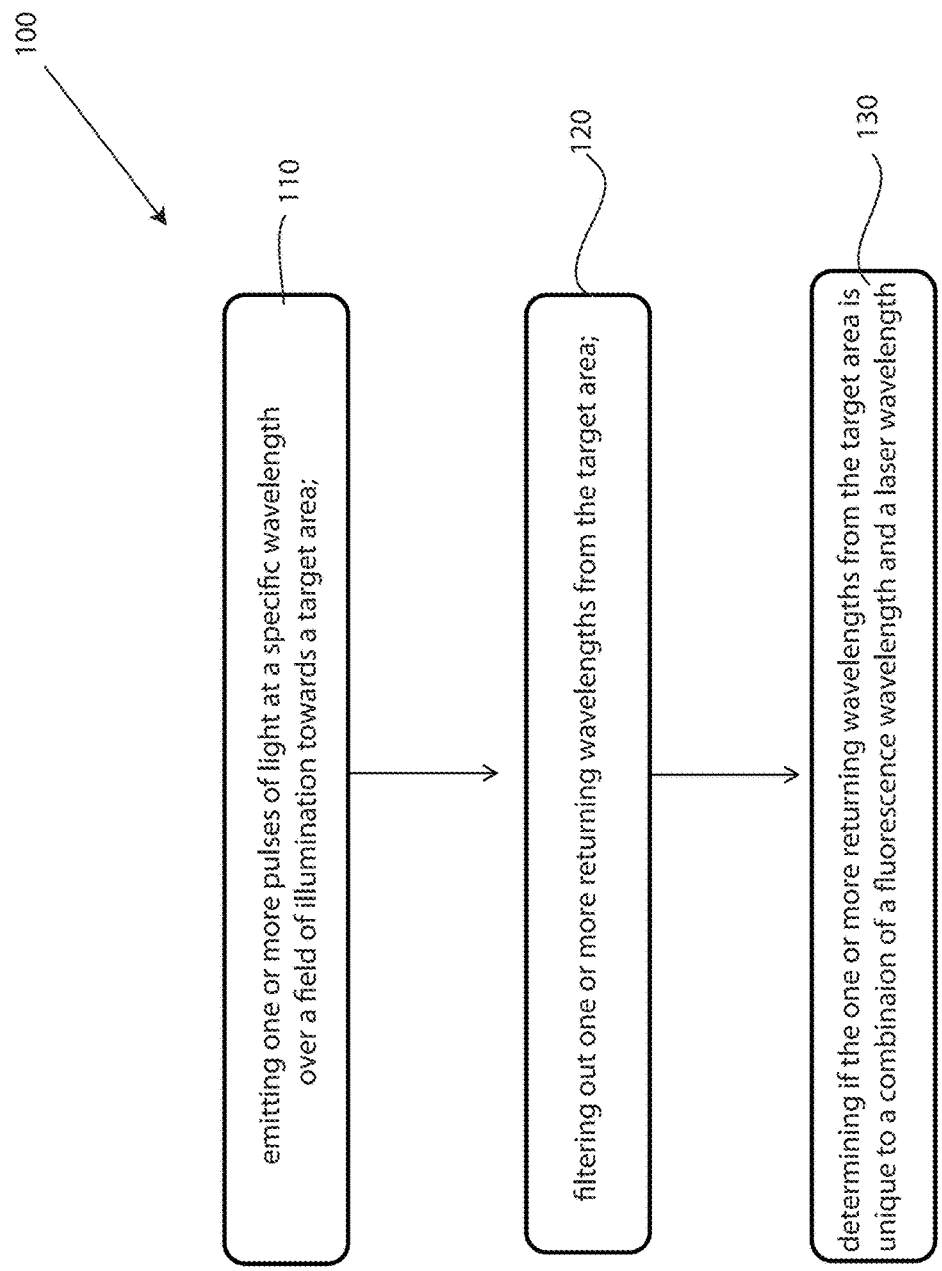
FIG. 1 depicts a flowchart showing an embodiment of a method.

Referring to the drawings, FIG. 1 depicts an embodiment of a method 100. Embodiments of method 100 may detect a biological signal behind a glass or similar reflective surface. For instance, embodiments of method 100 may be used for the detection of a human being behind a sniper rifle having a scope. Embodiments of method 100 may detect a biological signal, such as a biofluorescence signature from a human eye. Using method 100, a target area may be interrogated for sniper threats prior to a shot being fired. Embodiments of a target area may include an urban environment, a building, a field, a mountainside, a hotel, a structure having windows, a home, or any physical location or space that could possibly accommodate a sniper. Those having skill in the art should appreciate that the target area may be an area or physical space that includes one or more objects, such as a building, etc., or may be a single object or building of interest. Interrogation of the target area may include scanning the area with a laser or other light emitting source to detect, capture, and filter any incoming wavelengths. A unique combination of a source wavelength and a fluorescence wavelength may indicate the presence of a sniper threat—a human eye behind a scope of a sniper rifle. Detecting the unique combination of a source wavelength and a fluorescence wavelength can indicate a biological presence behind glass.

Embodiments of method 100 may include the steps of detecting a unique dual wavelength, the unique dual wavelength resulting from one or more pulses of light in a field of illumination, wherein the unique dual wavelength is a combination of a fluorescence wavelength and a laser wavelength. Further embodiments of method 100 may include the steps of emitting one or more pulses of light at a specific wavelength over a field of illumination towards a target area 100, filtering out one or more returning wavelengths from the target area 120, an determining, based on the filtering, if a combination of a fluorescence wavelength and a laser wavelength is present 130.

Embodiments of the step 110 of emitting one or more pulses of energy in a field of illumination towards a target area may be accomplished by an energy source 20 capable of emitting electromagnetic radiation. Embodiments of the energy source 20 may be an emitter, a laser, an industrial laser, a massive array of LEDs, a long range laser, a short pulse laser, a single wavelength laser, a precisely timed pulse laser, and the like. For example, embodiments of the energy source 20 may include a laser having more than one of these features or characteristics. Embodiments of the energy source 20 may emit non-visible electromagnetic radiation, such as UV light. Further embodiments of the energy source 20 may be an industrial laser with a single 25 nanosecond duration pulse with a 50 Hz rep rate. The energy source 20 may be used to scan, interrogate, probe, search, illuminate, etc., a target area from a distance. Distances from the energy source 20 to the target area may vary, and may be calculated by the energy source, using range finding capabilities of laser devices. In some embodiments, the distance from the energy source 20 to the target area can be 1000 meter, while still being effective at detecting a biological signature behind a glass surface. The energy source may be a pulses laser having a wavelength of 351 nm. Embodiments of a source wavelength may refer to the wavelength of energy emitted from the energy source 20. Thus, in one exemplary embodiment, the source wavelength may be 351 nm. However, those skilled in the art should appreciate that the source wavelength may have other wavelengths associated with non-visible light (or even visible light in some application, particularly, embodiments where stealth does not matter.

Figure 2:
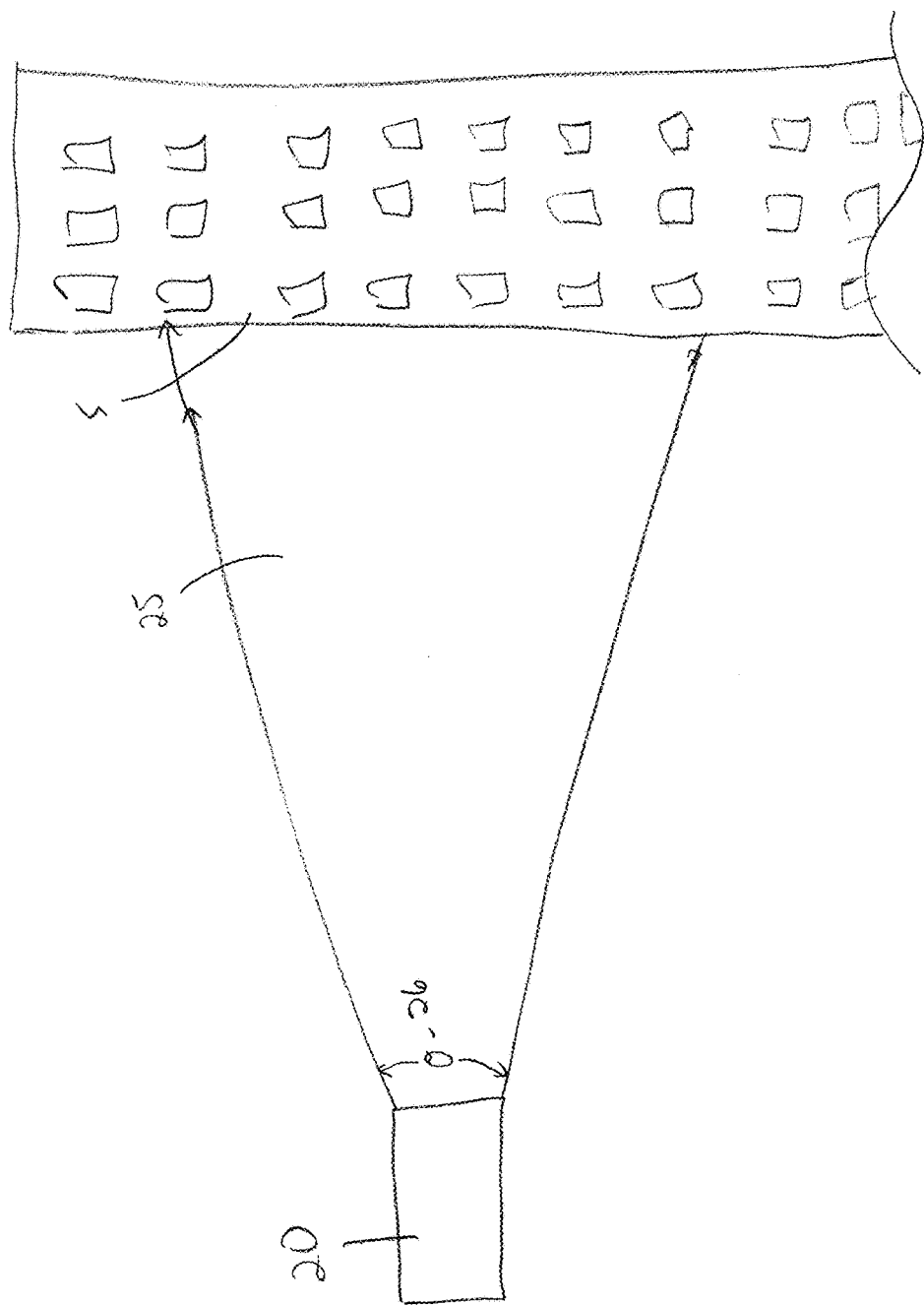
FIG. 2 is a schematic view of an embodiment of an energy source emitting an energy source towards a target area.

With reference now to FIG. 2, embodiments of the energy source 20 may be used to emit energy toward a target area 5 over a field of illumination 25. Embodiments of the field of illumination 25 may also be a field of view, a search field, a target field, field of vision, or an area covered by the emitted energy from the energy source 20. The field of illumination 25 may be determined by a beam spread angle 26, which can be the angle of the energy beam measured at the energy source 20. Embodiments of the beam spread angle 26 may vary according to the desired scope, size, and target area to be covered by the field of illumination 25. In one embodiment, the beam spread angle may be 2.3°. A broader range of the spread beam angle 26 is contemplated, such as a range between 1.1° to 3.5°. Even smaller or larger beam spread angles 26 may be used according to the size of the target area 5 to be scanned by the energy source 20. In one embodiment, the beam spread angle 26 may illuminate a 40 meter wide patch at one kilometer. This emitted signal may reflect off the optical surfaces of the optic device 15, wherein a brightest return comes from a focal point 16, such as the reticle.

Figure 3:
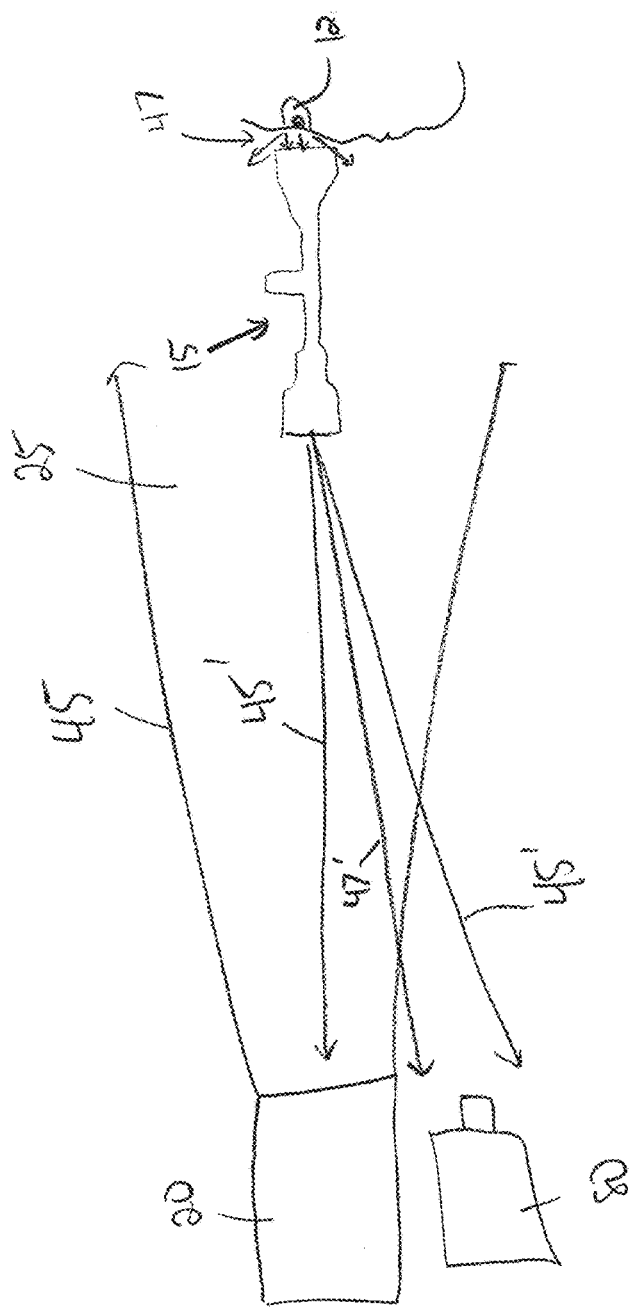
FIG. 3 depicts a schematic view of an embodiment of an energy source, a camera, an optic device, and a human eye behind the optic device.
Figure 4:
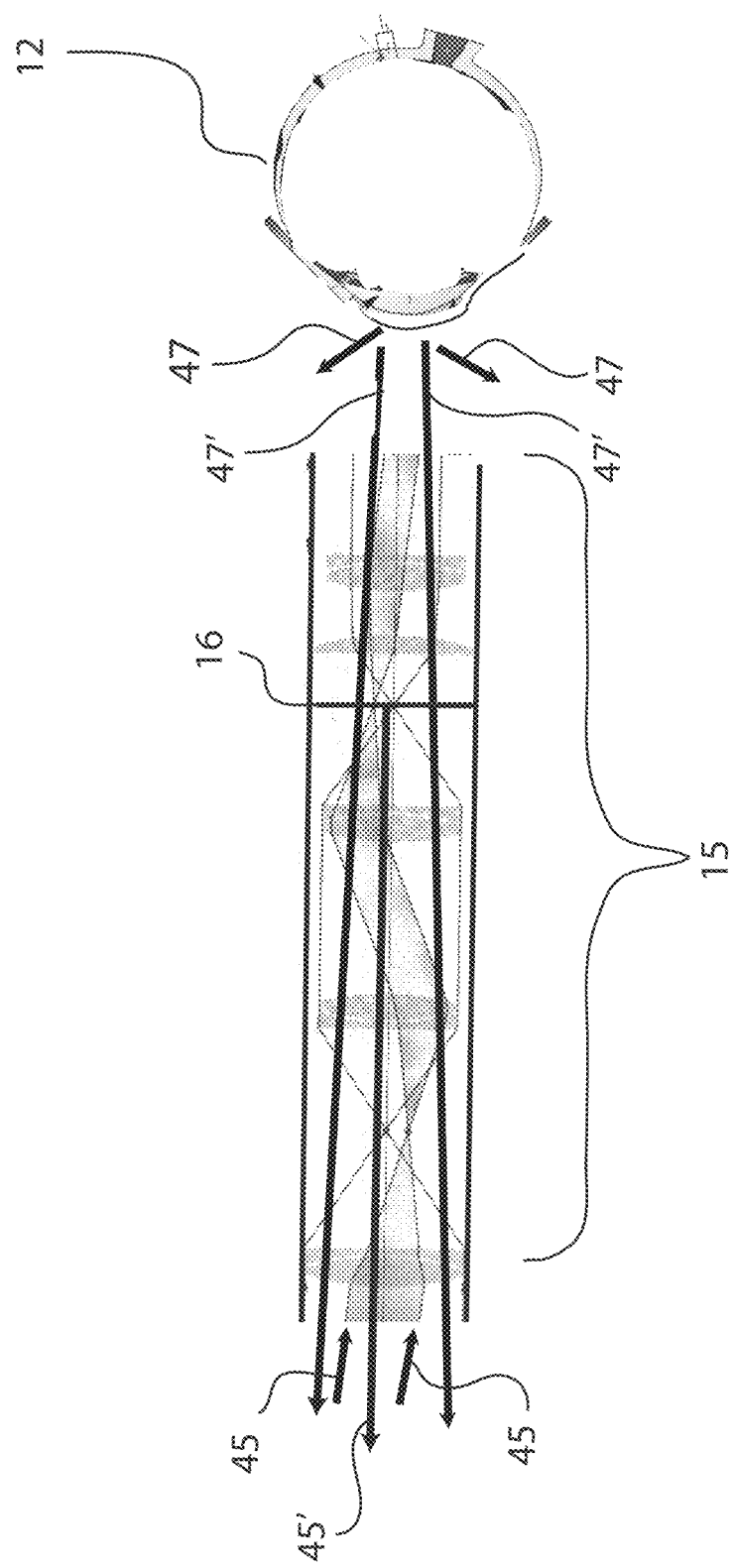
FIG. 4 depicts a schematic view of an embodiment of an optic device, and the return signals of the optic device and the human eye.

Referring now to FIG. 3, embodiments of method 100 includes generating a unique return from the emitted energy towards the target area 5. Embodiments of the unique return may include a fluorescent wavelength in combination with a source wavelength. Optical techniques can perform this detection, but isolating a specific detection to a sniper requires generating the unique return that could only be attributed to the sniper's optical chain. The approach described herein may take into account the entire optical chain; the resulting design concept allows a dual wavelength detection of both the sniper scope and the human eye behind it. Detecting the dual wavelength of a fluorescence wavelength 45' and a source wavelength 47' may result from the one or more pulses of energy in a field of illumination 25. Specifically, the pulsed energy 45 is projected, emitted, placed, directed, targeted, toward a target area 5, wherein a human eye 12 may be behind a optic device 15, as shown in FIG. 4.

Embodiments of the optic device 15 may be a rifle scope, a pair of binoculars, sunglasses, or a combination thereof. Embodiments of optic devices 15 may include a focal point 16, wherein the incoming light emitted by the energy source 20 at the focal or focus point 16 is retroreflected back towards an image capturing device 80. For instance, a focal point 16 of the optic device 15 may be a flat piece of glass associated with the optic device 15; the focal point 16 may be located at a flat portion of the magnifying lens of the optic device 15. The higher the magnification of the lens of the optic device 15, the stronger the return signal. The reflection of the emitted light at the focal point 16 of the optic device 15 may be highly directional, bright, and be considered retroreflected. In one embodiment, about 4%-8% of the emitted energy 45 will be reflected back towards camera 80 for analysis and detection. In other embodiments, at least 1% of the emitted energy, such as UV light, will be reflected back towards the camera 80. In yet another example, the total return signal of the optic device may include ghost returns from all the other pieces of glass in the scope and a 3% reflectivity for each air to glass interface of the cross hair window for a total of 6%, wherein 3% per surface is typical for a single layer MgF coating. In other words, the sniper scope detection may be based on a "cat's eye" retro-reflection off of the scope reticle (e.g. internal glass window holding cross hairs—focal point 16). Other optic devices 15, such as sunglasses and binoculars may have a focal point 16 as well. In the embodiment of a rifle scope, the focal point 16 may be located in an internal pathway of the scope, such as the piece of glass where the reticle may be etched. Optic devices 15 may include anti-reflective coating, but may still return a source wavelength.

Moreover, embodiments of the human eye 12 that may be located behind the optic device 15, or other glass surface, may convert the emitted energy 45 from the energy source 20 to a fluorescence wavelength 47. In other words, the emitted energy 45 may excite a protein of a lens of a human eye 12 that can convert the emitted energy 45 to a longer wavelength. For example, the human eye may bio-fluoresce and convert the emitted energy having a wavelength of 351 nm to 450 nm in roughly 2 nanoseconds. In other embodiments, the emitted source wavelength may be converted by 20 nm to 150 nm. The emitted energy 45 may travel through the optic device 15 and into the lens of the human eye. When the protein of the lens of the human eye is excited, a fluorescence wavelength 47 can radiate from the human eye 12; about 1%-4% of the pulsed energy delivered to the eye 12 may be fluoresced.

A small percentage of the radiating fluorescence 47 may be captured or received by the optic device 15 and travels back through an internal pathway of the optic device 15 (or through one or more glass surfaces of an optic device 15) towards camera 80. For example, sighting optics 15 in front of the eye 12 may collect a portion of radiating fluorescence 47 from a solid angle determined by the eye's iris and the sighting optics eyepiece. The sighting optics may then projects the fluorescent light 47' out of the sighting optics' objective where it can be detected at a distance by the camera 80. This technique may ensure that the sighting optics 15 used has an eye 12 behind it, preventing false alarms. In one exemplary embodiment, a minimum of 2% of the radiant fluorescence 47 travels back through the scope. The fluorescence radiation 47 that returns to the camera 80 is shown in FIGS. 3 and 4 as a fluorescence wavelength 47'. The emitted energy that is retroreflected from the focal point 16, or reticle in the case of a scope, is shown in FIGS. 3 and 4 as a source wavelength 45'. Accordingly, a specific signal return, or a dual wavelength may include the source wavelength 45' and a fluorescence wavelength 47.' The specific return signal may indicate a signature unique to a sniper eye and scope. For instance, a source wavelength of 351 nm, coupled with a fluorescence wavelength of 450 nm, can be unique to the sniper eye/scope combination, and can be strong enough to be readily detected with a dual wavelength, GenIII, solid state camera system, described in greater detail infra. In some embodiments, the return signal may only include a source wavelength 45.' Likewise, some embodiments of the signal return may only include a fluorescence wavelength 47.'

Some specific scenarios are discussed below in accordance with method 100:

For ease of communication, it is assumed that a blue source (source wavelength 45/45') and a green return (fluorescence wavelength 47') from the interrogation target human eye lens:

Sniper scope with human operator—The blue light focuses down to the rifle scope reticle and gives a relatively bright return almost identical to the effect of car headlights picking up the eyes of animals during night driving. On top of this blue return signal would be the green light from eye lens fluorescence. Color filters and gated intensified CCD cameras 80 can be used to detect and separate these two return signals.

Binoculars with human operator—Two side by side green return signals, very weak or non-existent blue return signal.

Shiny metal objects or vacant optics—No green return signal, blue only.

Spotter scope with human operator—Single green return signal, weak or non-existent blue return.

Sniper wearing sunglasses—Strong blue return from both the reticle and the sunglass lens next to the eyepiece, and weak, but detectable green return from the lens of human eye. Optimal source wavelength can be utilized to sneak past the cut-off wavelength of the sunglasses. Blue light blocking shiny sunglasses would give a very bright blue return. Near flat glass outside the eyepiece has the same effect as the flat reticle inside the sniper scope, but is much more reflective. This situation may drive the choice of the pulsed source laser wavelength.

Figure 5:
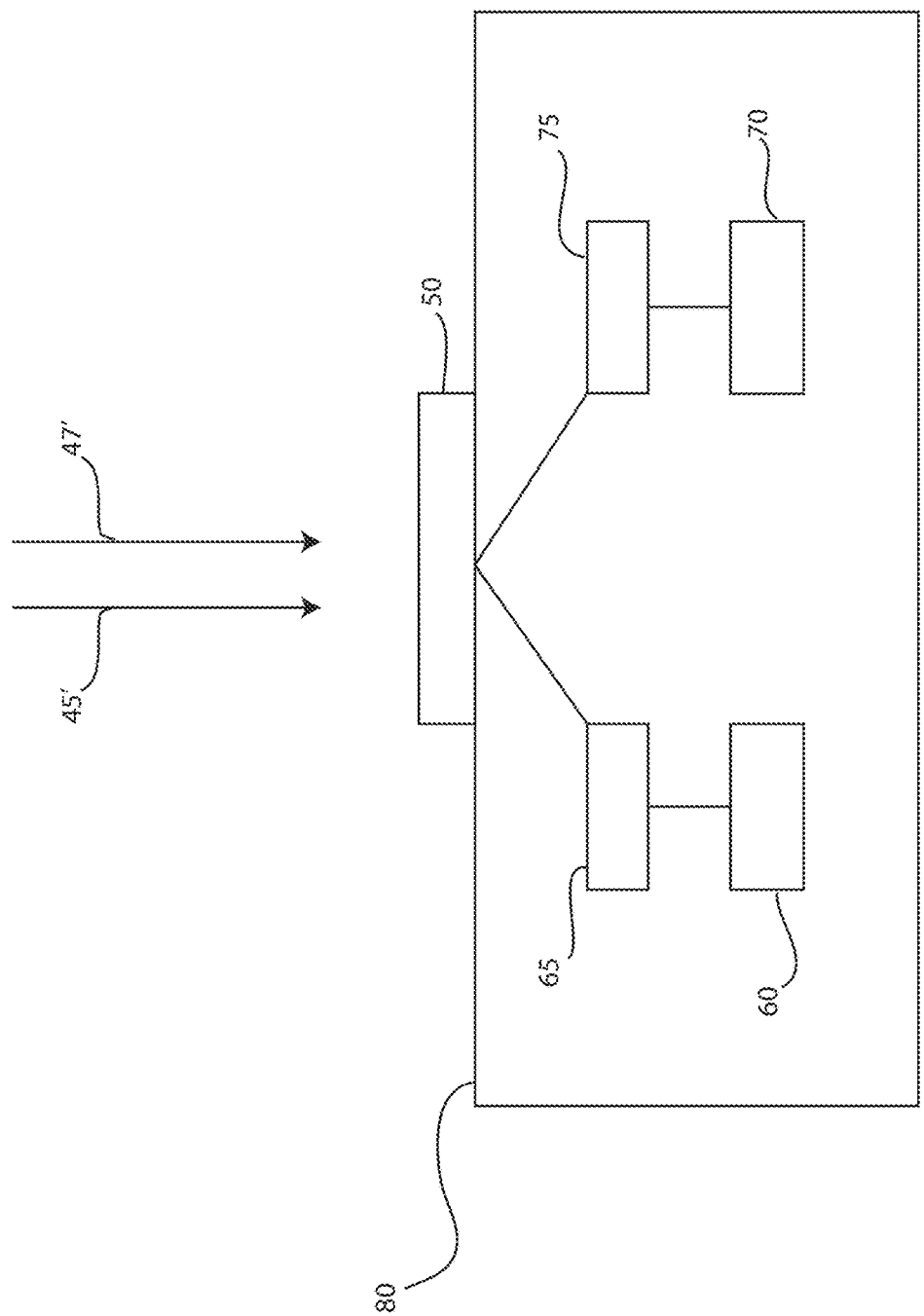
FIG. 5 depicts a schematic view of an embodiment of a camera 80.

Referring now to FIG. 5, and with reference again to FIG. 1, embodiments of method 100 include the step of filtering out one or more returning wavelengths from the target area 120. Embodiments of the one or more returning wavelengths may be collected, received, captured, etc. and filtered by a camera 80. Embodiments of camera 80 may be an image capturing device, an image processing device, an image storage device, an image collection device, or any electronic device that can filter, store, analyze information regarding the returning wavelengths of a target area 5. Furthermore, reflection of emitted energy 45 from sighting optic device 15 and background may be imaged by camera 80, wherein camera 80 may be synchronized to the energy pulse of the energy source 20.

Embodiments of the camera 8 may be coupled to a computing device having a processor. The camera 80 may include an internal computing device, or a dedicated internal computer, or may be coupled to a remote computing device. Embodiments of camera 80 may discriminate against ambient light. Embodiments of camera 80 may further include a 130 mm diameter lens, optical filters, gated GenIII intensifiers and CCDs or EMCCDs to capture images. The gating of the intensified imagers may minimize effects of background light when the return optical pulse is not present. The CCD may include a full well of 100,000 charge carriers, and an rms electronic noise floor of 10 charge carriers; the electronic read noise may be negligible in the field. The predominant noise sources may be the photo-cathode shot noise and micro-channel plate gain noise. Embodiments of camera 80 may have an operational speed of a frame rate of 14.3 per second; one having ordinary skill in the art should appreciate that other frame rates, faster and slower, may be used to implement method 100. Embodiments of the camera 80 may also be carefully timed with the laser; the camera 80 may be synchronized with the energy source 20. The gating of the camera 80 may result in an on/off for a ¼ or ½ second interval; other gating intervals may be practiced.

Furthermore, embodiments of camera 80 may include a beam splitter 50 to separate the returning wavelengths, a first bandpass filter 65 associated with a first camera system 60, a second bandpass filter 75 associated with a second camera system 70. Embodiments of the beam splitter may split the returning wavelengths, for example, source wavelength 45' and fluorescence wavelength 47.' Embodiments of the beam splitter may be a filter, such as a dichroic filter. In an exemplary embodiment, the beam splitter 50 or optical filter, such as dichroic filter, may pass the source wavelength 45' and reflect or transmit the fluorescence wavelength 47' to the side toward the second bandpass filter or second camera system 70, or vice versa. Moreover, embodiments of camera 80 may be a two camera device, wherein two camera systems comprise camera 80. The first camera system 60 may be associated with the source wavelength 45. The second camera system 70 may be associated with the fluorescence wavelength 47.' For instance, the first camera system 60 may utilize the bandpass filter 65 that may be tuned to the wavelength of the source wavelength 45,' while the second camera system 70 may utilize bandpass filter 75 that may be tuned to the wavelength of the fluorescence wavelength 47.' Alternatively, embodiments of the camera 80 may simply have two bandpass filters and image capture and storing capacities within the single camera, but do not need to be separate systems. Accordingly, the camera 80, or the first camera system 60 and the second camera system 70 of camera 80, may digitally store images for analysis and determination of whether both the source wavelength 45' and the fluorescence wavelength 47' is present in the target area.

Figure 6:
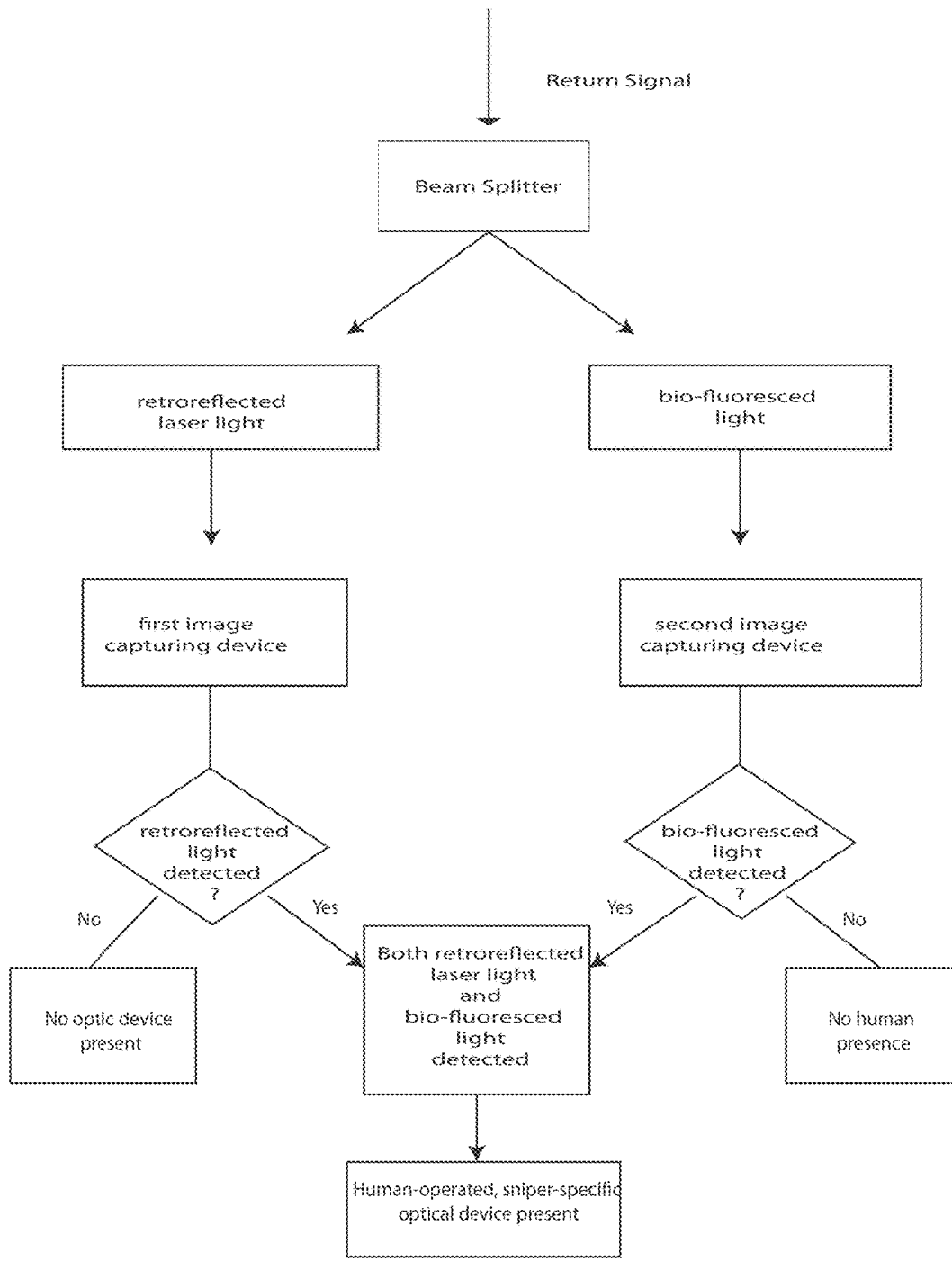
FIG. 6 depicts a flow chart showing how to determine if a unique signal return is present in a target area.

Specifically, FIG. 6 depicts a flow chart for the step of determining, based on the filtering, if a combination of a fluorescence wavelength and a laser wavelength is present 130. First, the returning signal(s) may be separated or filtered by wavelength. The first camera system 60 may determine if any retroreflected light is detected in the target area. For instance, the first camera system 60 may produce and/or store an image at the source wavelength. A "spot" or other indicator may be presented or displayed to an operator to indicate a presence of the source wavelength 45.' The decision to present or display a "spot" or other indicator may follow a yes/no logic to a question similar to—is the source wavelength present in the target area? If no return retroreflected light is detected, then it is likely that no optic device 15 is present in the target area, and no "spot" or indicator is displayed or presented. Likewise, the second camera system 70 may determine if biofluoresced light is detected in the target area. For instance, the second camera system 70 may produce and/or store an image at the fluorescence wavelength. A "spot" or other indicator may be presented or displayed to an operator to indicate a presence of the fluorescence wavelength 47.' The decision to present or display a "spot" or/ other indicator may follow a yes/no logic to a question similar to—is a fluorescence wavelength 47' present in the target area? If no return fluoresced light is detected, then it is likely that there is no biological presence, such as a human eye, in the target area. However, if the camera 80, or the first and second camera systems 60, 70, determine that both the return source light is present and the fluoresced light is present, then it is likely that a human-operated, sniper-specific optical device is present in the target area 5. Two "spot" or indicators may be displayed or presented to the operator to notify the operator that the unique biological signature has been detected in combination with an energy source 20 wavelength.

Furthermore, an image stored by camera 80 may have a pixel associated with a number, and each pixel may hold a number of electrons. For example, each pixel may hold 100,000 electrons. The return signals may be resulting in about 20-30 electrons. Therefore, the images may be stacked to smooth out the electronic noise. Stacking may refer to multiples pulses of energy from the energy source towards the same target area 5. Each time the returning signal is processed by the camera 8 or other computing device, the number of electrons may be increased for each pixel because the images are stacked on each other. Prior to emitting the energy pulse towards the target area 5 with the energy source 20, method 100 may include the step of taking one or more snapshots of a background of the target area 5. For instance, four background snapshots may be taken of the background of the target area 5 before emitting the energy toward the target area 5. Then after the one or more pulses of the energy source 20 against the target area 5, the background may be subtracted from the digitally processed image.

Examples

An analysis was done of three expected sniper signatures at 1 km, an anticipated background signal, and an anticipated counter measure.

Analysis Results

TABLE 1

Optical Return Signals from Sniper Scope & Eye Lens

| sniper configuration | UV Pump Beam Return | Blue Eye Lens Return |
|---|---|---|
| Iris > 4.2 mm dia. (at dusk) | 1200 electrons | 47,500 (½ CCD full well) |
| 3 mm diameter iris | 1200 electrons | 24,300 electrons |
| Sunglasses, 30% trans | >1200 electrons | 4,300 electrons |

Noise ratios range from 7% for the strongest signal to 29% for 1200 electrons. These images are on "top" of the unsynchronized background images captured and stored for post processing. Two situations were analyzed for comparison with the laser pulse returns: a bright blue sky (possible silhouette condition) and a high power narrow beam head lamp.

TABLE 2

Un-synchronized Signals from Sky and Headlamp

| Background Countermeasures | UV Signal | Blue Signal |
|---|---|---|
| Bright Blue Sky | 87 electrons | 164 electrons |
| Narrow Beam Headlamp | 402 electrons | 10,200 electrons |

The noise levels for the Headlamp are 50% for the UV Camera and 11% for the Blue Camera. It is anticipated that these images would be taken before the laser pulse(s) while a range finder is operating to set the camera shutter delays. The bright sky signals are almost negligible due to the 25 ns time gate and 10 nm optical filter bandwidth. The headlight modeled for this analysis has a 1300 lumen output with 50% power inside a 167 meter diameter circle at 1 km. Additional performance is realized utilizing signal processing techniques including spatial correlation techniques for the direct reflection and fluorescent images.

Additionally, a possible processing sequence, with half the sample noise, could be as follows: Counter sniper team selects target location to scan, four background frames are captured and stored digitally (550 millisecond.) while the range finder calculates range and sets the camera shutter delay, four laser pulses are emitted and four target image pairs are taken and stored (550 millisecond.), and the 4-stack background image is subtracted from the 4-stack pulse return image. A "blue" image threshold test may determines if an eye is behind the scope, and a UV to blue ratio test may determine if the scope has a reticle. If yes to both, a potential sniper has been detected. Estimated time: 1.2 seconds for the entire 40 meter square field of view at 1 km.

This is one of several image processing approaches that could yield a high probability of detection. The above sequence can be sped up by using the CCD "crop" mode of the chosen camera. With this operational flexibility 10 selected pixel rows can be read out in 3 milliseconds to yield a high post processing rate set by laser performance for regions of interest. This may allow a very rapid scan of a row of building windows in 80 milliseconds, for example.

Other eye phenomena may be utilized in a similar manner to minimize false alarms associated with optics reflection only. These phenomena include retina/macula reflection and fluorescence. The complete system would include the electro-optic equipment described, light beam elevation and bearing control and measurements and GPS absolute position measurements, which, combined with the afore-mentioned laser rangefinder, would provide a complete fire control solution.

Referring back to FIG. 1, embodiments of method 100 may be coupled with other elements. For example, method 100 may be implemented with a vehicle mounted system, and have the following features: Gimbaled scanning assembly covering an area of regard, 1000 m detection range with 2.3° FOV, 40 m diameter coverage area at 1km in <0.5 seconds, tunable for lesser ranges, detectable eye—optic combinations with RedEye in its field of view, multiple pump frequencies to address foreseen countermeasures.

Figure 7:
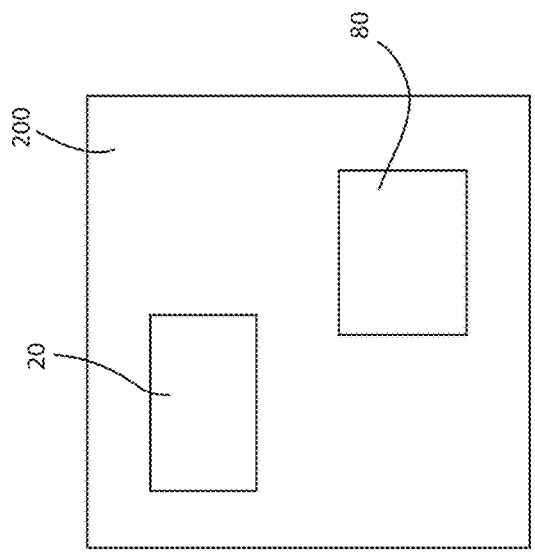
FIG. 7 depicts a schematic view of an embodiment of a system.

Embodiments of method 100 may also be implemented by one or more components of system 200, as show in FIG. 7. For example, system 200 may include an energy source 20 for emitting one or more pulses of energy at a specific wavelength over a field of illumination 25 towards a target area 5, an image processing device 80 having a first image processing device 60 for receiving a returned source wavelength 45', and a second image processing device 70 for receiving a returned fluorescence wavelength 47', wherein the image processing device 80 determines if both the returned source wavelength 45' and the returned fluorescence wavelength 47' are present while scanning the target area.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

what is claimed is:

1. A method comprising:
providing an energy source and an image processing device for detecting a biological signature of an eye of a person behind a glass surface using non-visible light, the biological signature is a biofluorescence wavelength converted from a wavelength of the non-visible light when the non-visible light excites a protein of a lens of the eye of the person behind the glass surface, wherein the excitation of the protein of the lens of the eye is is imperceptible to the person;
detecting a retroreflected wavelength of the energy source in addition to the biofluorescence wavelength; and
distinguishing between the retroreflected wavelength and the biofluorescence wavelength to confirm a presence of a human-operated sniper specific optical device.

2. The method of claim 1, wherein the glass surface is at least one of a lens of an optics device, a lens of sunglasses, and a lens of a binocular.

3. The method of claim 1, wherein the non-visible light is UV light from the energy source.

4. A method comprising:
emitting one or more pulses of energy at a specific wavelength over a field of illumination towards a target area;
filtering out one or more returning wavelengths from the target area;
determining, based on the filtering, if a combination of a biofluorescence wavelength and a retroreflected source wavelength is present; and
distinguishing between the retroreflected source wavelength and the biofluorescence wavelength to confirm to confirm a presence of person operating an optics system.

5. A method comprising:
capturing a unique dual wavelength by an image processing device, the unique dual wavelength resulting from one or more pulses of energy in a field of illumination emitted by an energy source, wherein the unique dual wavelength captured by the image processing device is analyzed to determine that the unique dual wavelength includes a biofluorescence wavelength separate from a retroreflected source wavelength; and
confirming a presence of a person operating an optics system without alerting the person.

6. The method of claim 5, wherein the biofluorescence wavelength is generated by a biofluorescence of a human eye when excited by the one or more pulses of energy.

7. The method of claim 5, wherein the retroreflected source wavelength is generated by a retro-reflection off of a reflective surface of an optic device.

8. The method of claim 5, wherein the biofluorescence wavelength has a wavelength of 450nm and the laser wavelength has a wavelength of 351nm.

9. The method of claim 5, wherein the energy is UV light.

10. The method of claim 4, wherein the step of filtering is accomplished by a dichroic filter.

11. The method of claim 4, wherein an energy source emits the one or more pulses of energy.

12. The method of claim 11, wherein the energy source is a UV light source.

13. The method of claim 4, wherein the biofluorescence wavelength is generated by a biofluorescence of a human eye when excited by the one or more pulses of energy.

14. The method of claim 4, wherein the retroreflected wavelength is generated by a retro-reflection off of a reflective surface of an optic device.

15. The method of claim 4, wherein the target area is located within an urban environment.

16. A system comprising:
an energy source for emitting one or more pulses of energy at a specific wavelength over a field of illumination towards a target area;
an image processing device having a first image processing device for receiving a returned source wavelength, and a second image processing device for receiving a returned biofluorescence wavelength;
wherein the image processing device determines if both the returned source wavelength and the returned fluorescence wavelength are present while scanning the target area;
wherein the returned source wavelength is generated by a retro-reflection off of an optics system located in the target area;
wherein an excitation of a protein of a lens of an eye is imperceptible to a person, the excitation caused by the one or more pulses of energy;
wherein the returned source wavelength is detected in addition to the biofluorescence wavelength and distinguished between the returned source wavelength and the biofluorescence wavelength to confirm a presence of a human-operated sniper specific optical device.

17. The system of claim 16, wherein the energy source is a UV light source.

18. The system of claim 16, wherein the fluorescence wavelength is generated by a biofluorescence of a human eye when excited by the one or more pulses of energy.

* * * * *

UNITED STATES PATENT AND TRADEMARK OFFICE
CERTIFICATE OF CORRECTION

PATENT NO.         : 9,995,685 B2                          Page 1 of 1
APPLICATION NO.    : 15/340685
DATED              : June 12, 2018
INVENTOR(S)        : Jeffrey Michael Smith et al.

It is certified that error appears in the above-identified patent and that said Letters Patent is hereby corrected as shown below:

In the Claims

Column 10, Lines 2-3:
Delete "to confirm to confirm" and insert -- to confirm --

Signed and Sealed this
Fifteenth Day of January, 2019

Andrei Iancu
*Director of the United States Patent and Trademark Office*